US012251510B2

(12) United States Patent
Smaldone et al.

(10) Patent No.: US 12,251,510 B2
(45) Date of Patent: Mar. 18, 2025

(54) BREATH-ENHANCED NEBULIZER FOR DELIVERY OF AEROSOLIZED DRUGS TO VENTILATED PATIENTS

(71) Applicants: The Research Foundation For The State University of New York, New York, NY (US); Inspirx, Inc., Durham, NC (US)

(72) Inventors: Gerald Smaldone, Stony Brook, NY (US); Rohinton Toddywala, Somerset, NY (US); Akanksha Hande, Somerset, NY (US); Vijay Shukla, Somerset, NY (US)

(*) Notice: Subject to any disclaimer, the term of this patent is extended or adjusted under 35 U.S.C. 154(b) by 868 days.

(21) Appl. No.: 16/972,166

(22) PCT Filed: Jun. 6, 2019

(86) PCT No.: PCT/US2019/035856
§ 371 (c)(1),
(2) Date: Dec. 4, 2020

(87) PCT Pub. No.: WO2019/236896
PCT Pub. Date: Dec. 12, 2019

(65) Prior Publication Data
US 2021/0361896 A1    Nov. 25, 2021

Related U.S. Application Data

(60) Provisional application No. 62/681,654, filed on Jun. 6, 2018.

(51) Int. Cl.
*A61M 11/06* (2006.01)
*A61M 11/00* (2006.01)
(Continued)

(52) U.S. Cl.
CPC ............ *A61M 11/06* (2013.01); *A61M 11/00* (2013.01); *A61M 15/0095* (2014.02);
(Continued)

(58) Field of Classification Search
CPC .. A61M 15/0095; A61M 11/00; A61M 11/06; A61M 16/0057; A61M 16/04;
(Continued)

(56) References Cited

U.S. PATENT DOCUMENTS 3,733,060 A * 5/1973 Merritt .................. B01F 25/316
261/DIG. 65
5,054,477 A * 10/1991 Terada ................ A61M 16/125
128/200.22
(Continued)

FOREIGN PATENT DOCUMENTS

EP          3810235 B1     12/2023
WO    WO-2004045690 A1 *  6/2004  ............ A61M 15/00

OTHER PUBLICATIONS

Inhaled Colistin (Year: 2016).*

Primary Examiner — Joseph D. Boecker
(74) Attorney, Agent, or Firm — Andrew H. Berks (57) ABSTRACT

A breath-enhanced nebulizer adapted for use in administering an aerosolized pharmaceutical composition to a patient by inhalation wherein the patient is connected to a mechanical ventilator is disclosed. The nebulizer has a Venturi driven by a nebulizer air supply that draws a solution of a pharmaceutical composition into a shear zone where the solution is atomized. The Venturi effect is amplified by the internal configuration of the nebulizer to increase the rate of nebulization of drug. Optionally, breath-actuated nebulization is used, employing a pressure sensor interposed between the nebulizer and mechanical ventilator that controls the nebulizer air supply, such that nebulizer air and concomitant
(Continued)

nebulization only occurs during the inhalation phase of a breathing cycle.

12 Claims, 12 Drawing Sheets (51) Int. Cl.
    *A61M 15/00*     (2006.01)
    *A61M 16/00*     (2006.01)
    *A61M 16/04*     (2006.01)
    *A61M 16/08*     (2006.01)
    *A61M 16/14*     (2006.01)
    *A61M 16/20*     (2006.01)

(52) U.S. Cl.
    CPC ........ *A61M 16/0057* (2013.01); *A61M 16/04* (2013.01); *A61M 16/0883* (2014.02); *A61M 2016/0027* (2013.01); *A61M 16/0875* (2013.01); *A61M 16/147* (2014.02); *A61M 16/204* (2014.02); *A61M 2205/3331* (2013.01); *A61M 2206/20* (2013.01)

(58) Field of Classification Search
    CPC .......... A61M 16/0463; A61M 16/0883; A61M 16/14; A61M 16/16; A61M 2016/0027; A61M 2205/3331; A61M 2206/20; A61M 16/127; A61M 16/0816; A61M 16/0875; A61M 16/147; A61M 16/20; A61M 15/0086; A61M 15/0091; A61M 15/0005; A61M 15/002; A61M 15/0098; A61M 16/0003; A61M 16/204

See application file for complete search history.

(56) References Cited

U.S. PATENT DOCUMENTS

| | | | | |
|---|---|---|---|---|
| 5,062,419 A | * | 11/1991 | Rider | A61M 16/16 128/200.14 |
| 5,322,057 A | * | 6/1994 | Raabe | A61M 15/00 128/204.26 |
| 5,388,571 A | * | 2/1995 | Roberts | A61M 16/16 128/205.12 |
| 6,929,003 B2 | * | 8/2005 | Blacker | B05B 7/0012 128/207.14 |
| 2002/0026940 A1 | * | 3/2002 | Brooker | A61M 16/0833 128/204.23 |
| 2003/0005929 A1 | * | 1/2003 | Grychowski | A61M 15/0091 128/203.12 |
| 2015/0202398 A1 | * | 7/2015 | Fiorenza | F17D 5/005 137/544 |
| 2019/0241642 A1 | * | 8/2019 | Lefkowitz | C07K 14/70571 |

* cited by examiner

FIG. 1

PRIOR ART

○ Air from inspiratory line of ventilator
▓ Compressed Air
● Aerosol Particles

○ Air from inspiratory line of ventilator
◐ Compressed Air
● Aerosol Particles

PRIOR ART

FIG. 15

BREATH-ENHANCED NEBULIZER FOR DELIVERY OF AEROSOLIZED DRUGS TO VENTILATED PATIENTS

CROSS REFERENCE TO RELATED APPLICATIONS

This application is a national stage patent application filed under 35 U.S.C. § 371 of PCT International patent application PCT/US2019/035856, filed Jun. 6, 2019, and claiming priority to U.S. patent application 62/681,654, filed Jun. 6, 2018, the entire contents of each of which are incorporate by reference.

FIELD OF THE INVENTION

This invention pertains to a breath-enhanced nebulizer for use on a ventilator circuit for the administration of nebulized medications to patients connected to a mechanical ventilator.

BACKGROUND

The administration of nebulized drugs to patients on a mechanical ventilator is an important medical need. Challenges in the administration of nebulized drugs to patients on a medical ventilator include maximizing efficient delivery of the drug to the lungs of the patient and provision of properly humidified breathing gases. Inefficient drug delivery wastes drug product, which may be expensive, may cause unpredictable dosing to patients (too much or too little drug) and may cause undesirable exposure of drug to surrounding persons. As used herein, the term "nebulized" is also referred to as "atomized" or "aerosolized," and all three terms are interchangeable.

Prior art approaches to administering nebulized drugs to patients on a ventilator typically involve nebulizers. In some cases, special nebulizers have been designed to mate with specific ventilators. In many cases, these nebulizers atomize the medication continuously, even during portions of the breathing cycle when the patient is not inhaling. Studies have shown the efficiency of prior art nebulizers is excessively variable resulting in unpredictable dosing of the drug to the lungs of the patient. (J. L. Rau, et al., "Performance Comparison of Nebulizer Designs: Constant-Output, Breath-Enhanced, and Dosimetric," Respir Care 2004, 49(2), 174-179). A breath-enhanced nebulizer was previously disclosed in WO2018/045263A1, published Mar. 8, 2018.

Nebulized aerosol delivery during mechanical ventilation can result in profound unregulated aerosol losses, which are a strong function of duty cycle or the inhalation-exhalation (I/E) ratio, ventilator bias flow, and humidification. This disclosure provides a novel nebulizer that minimizes these influences by utilizing a design that results in aerosol generation primarily during inspiration (breath-enhancement) and minimizes expiratory losses (breath-actuation).

SUMMARY OF THE INVENTION

Disclosed is a breath-enhanced jet nebulizer configured to aerosolize small drug volumes and deliver size-specific aerosol particles, while recycling larger aerosol particles in the nebulizer that would not be effectively reach the alveolar region of the lungs. The recycled liquid can be re-aerosolized to form smaller particles for delivery to the lungs. In an embodiment, the inventive nebulizer is in fluid communication with the inspiratory output port of a mechanical ventilator that controls the breathing cycle of a patient. In an embodiment, the air flow from the mechanical ventilator enhances the nebulization of the drug solution, meaning that the rate of nebulization is increased. In an embodiment, a pressure sensor is configured to toggle the nebulization, so that nebulization only occurs when the ventilator is in an inhalation phase of a breathing cycle.

In an embodiment, a breath-enhanced nebulizer is disclosed, adapted for use in administering a nebulized pharmaceutical composition to a patient by inhalation wherein the patient is connected to a mechanical ventilator. The nebulizer includes a housing with a breathing gas channel, wherein the breathing gas channel comprises an inlet in fluid communication with a mechanical ventilator and an outlet in fluid communication with a patient interface, and wherein breathing gases flow from the inlet to the outlet when the ventilator is in an inhalation phase of a breathing cycle. The breathing gas channel further comprises a Venturi section having a constriction in the gas channel, and wherein a nebulizer air jet and a liquid orifice are co-located in the Venturi section, and wherein the liquid orifice is in fluid communication via a liquid channel with a pharmaceutical composition solution in a reservoir. A nebulizer air flow at the air jet creates a Venturi effect that draws the pharmaceutical composition solution through the liquid channel to the liquid orifice. The pharmaceutical composition solution is directed towards the air jet such that the pharmaceutical composition solution is nebulized by contact with the air jet. The breathing gases, during an inhalation, enhance the Venturi effect to increase the rate of flow of pharmaceutical composition solution to the liquid orifice. After the pharmaceutical composition is nebulized, the nebulized composition is carried by the breathing gas flow to the patient interface. In an embodiment, the breathing gas flow through the nebulizer is the exclusive source of breathing gases delivered to the patient.

In an embodiment, a baffle is positioned proximal to the air jet and liquid orifice, such that the pharmaceutical composition solution and air jet are both aimed at the baffle.

In an embodiment, the patient interface is an endotracheal tube.

In an embodiment, a pressure sensor is interposed between the nebulizer inlet and the mechanical ventilator, wherein the pressure sensor is in electronic communication with a solenoid valve that controls the flow of nebulizer air to the nebulizer air jet, such that nebulizer air only flows during an inhalation phase of a breathing cycle.

In an embodiment, the nebulizer air flow and concomitant nebulization is continuous.

In an embodiment, a means is provided for continuous addition of pharmaceutical composition solution to the reservoir, for example by using a special port allowing the pharmaceutical composition solution to be added continuously to the solution reservoir.

In an embodiment, a method is disclosed for administering a nebulized drug to a patient breathing with a breathing circuit on a mechanical ventilator comprising nebulization of a drug with the apparatus as described above.

Figure 12:
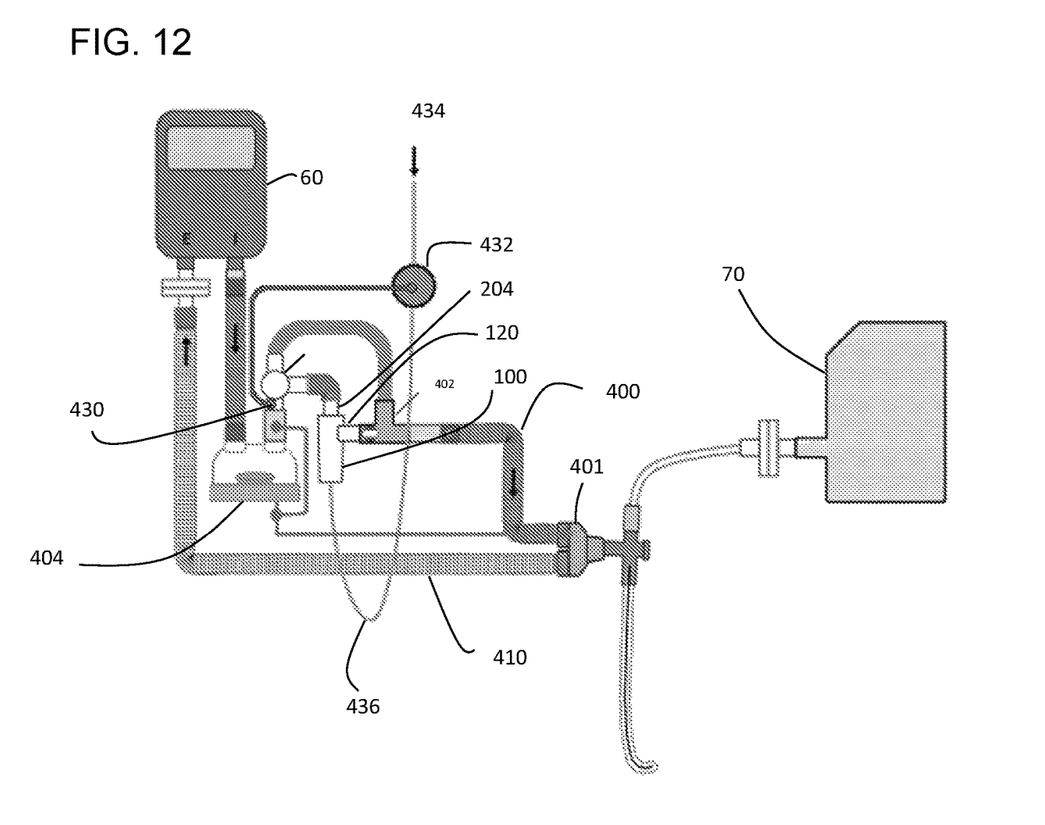
FIG. 12 is a representative ventilator circuit showing the mechanical ventilator, the patient, the nebulizer, and various other parts.

DETAILED DESCRIPTION

Disclosed herein is a "breath-enhanced" or "breath amplified" nebulizer for use with a mechanical ventilator. Essentially, this apparatus has a double Venturi effect, wherein the nebulization is caused by a vacuum created from a primary Venturi effect that draws a liquid drug solution through a liquid passage to an air jet, where the liquid impinges on a baffle and is nebulized. A secondary Venturi effect is created from the interior configuration of the gas passages in the apparatus, that enhances (or amplifies) the low-pressure zone around the Venturi jet to increase the flow of drug solution through the liquid passage. This secondary effect increases the rate of nebulization. In an embodiment, this apparatus is specifically designed to work with a mechanical ventilator that controls the breathing of a patient breathing through an endotracheal tube. Many different brands and styles of mechanical ventilators are in use today. All of them have features that control the breathing of patients in need of assisted breathing and control the inhalation and exhalation of the breathing cycle. In addition, mechanical ventilators supply breathing gases besides ordinary air, in particular oxygen enriched breathing gases for patients in need of supplemental oxygen. A particular feature of the inventive nebulizer is that it can operate independent of the specific brand of mechanical ventilator in use.

A conventional nebulizer is shown schematically in FIG. 1. This drawing shows a nebulizer body 10 with an inspiratory limb (conduit) 23 that carries aerosolized drug in breathing gases to the patient. Breathing gases or air enter the nebulizer from inlet limb 20. A drug solution reservoir 22 contains a liquid drug solution. A nebulizer air inlet 21 directs pressurized air (typically about 50 psi) to air jet 30. The air jet 30 creates a localized Venturi effect that draws the liquid drug solution through liquid inlet 24. When the liquid exits the inlet at liquid outlet 30, the liquid impinges on the baffle 28 and pressurized air flow from jet 30 and is nebulized, i.e., atomized in microdroplets that are suspended in the interior of the nebulizer 10 and carried away to the patient during an inhalation. A baffle 28 assists blocking large droplets from being inhaled and returning the liquid from large droplets to the reservoir.

The nebulizer in this invention incorporates several improvements over the design depicted in FIG. 1. A schematic of key features of the inventive nebulizer is shown in FIG. 2. The breathing gas channel spans the inlet 51 to outlet 52 and encompasses three regions. The inlet region 51 receives a breathing gas supply from a mechanical ventilator 60 and generally has a higher pressure ($P_1$) than outlet region 52 ($P_2$). Therefore, the flow of breathing gases will be from $P_1$ to $P_2$. Interposed between $P_1$ and $P_2$ is Venturi 53 ($P_0$), which has an even lower pressure than $P_2$, caused by the constriction in section 53 of the breathing passage. The low pressure at $P_0$ draws the drug solution 57 through draw tube 56. The drug solution exits tube 56 at liquid outlet 58 and is nebulized in the jet 55. The nebulized liquid is then carried away through section 52 to the patient 70.

The transport of the drug solution in FIG. 2 from reservoir 57 to liquid outlet 58 can be expressed by:

$$Q = \frac{P_W - P_0}{r} \qquad \text{Eq. 1}$$

Where Q is the flow rate, Pw is the pressure in the reservoir, normally atmospheric pressure, $P_0$ is the pressure in the Venturi at 53, and r is the flow resistance in tube 56.

The enhancement feature of this invention is an amplification of the pressure reduction, caused by the secondary Venturi effect noted above, from the air flow from the mechanical ventilator. $P_0$ is proportional to the inverse of the linear velocity of gases in the Venturi section:

$$P_0 \propto \frac{1}{V} \qquad \text{Eq. 2}$$

Here, the constriction in section 53 of the nebulizer increases the linear velocity V of the gases in section 53, and thereby decreases the pressure $P_0$ in that section, which in turn increases the flow rate Q in Eq. 1. In fact, the inventors found that the inventive nebulizer, as described herein, increased the rate of nebulization of 3 mL of drug solution from 60 mins in a conventional nebulizer to 14 mins in a breath-enhanced nebulizer.

In an embodiment, the breathing gas flow through the nebulizer is the only source of breathing gases supplied to the patient. However, this feature only applies when the breathing gas flow is directed to the inventive nebulizer. In an embodiment, the nebulizer can be bypassed by the ventilator circuit, in which case the breathing gases obviously are not going through the nebulizer.

In an embodiment as shown in FIG. 12, the inventive nebulizer (100) is shown as part of a complete ventilation circuit. In this representative schematic, mechanical ventilator 60 is in fluid communication with the inlet port 204 of nebulizer 100, with a humidifier 420 interposed between the nebulizer and the ventilator 60. Also shown are appurtenant parts such as a three-way valve, a T-Connector, and a bypass conduit. Inspiratory limb 400 and expiratory limb 410 are shown.

Also shown in FIG. 12 is pressure sensor 430, in electronic communication with solenoid valve 432 that controls the air flow from compressed air supply 434 to nebulizer air supply hose 436 that drives the nebulizer air jet in the nebulizer. In this configuration, the pressure sensor is triggered when breathing gas pressure at inlet 204 increases during the inhalation phase of the breathing cycle controlled by the ventilator. This is the embodiment in which the nebulization is breath-actuated. In an embodiment, the pressure sensor triggers nebulizer jet air flow only during the inhalation phase of the breathing cycle. Thus, with breath-actuation, no nebulization occurs during parts of the breathing cycle when the patient is exhaling or neither exhaling or inhaling. By placing the pressure sensor in this configuration, the breathing actuation control is completely independent of the brand or type of mechanical ventilator.

As described in FIGS. 3-11, an exemplary nebulizer is illustrated. In an embodiment, this nebulizer is adapted for use in administering an aerosolized pharmaceutical composition to a patient by inhalation wherein the patient is connected to a mechanical ventilator.

Figure 3:
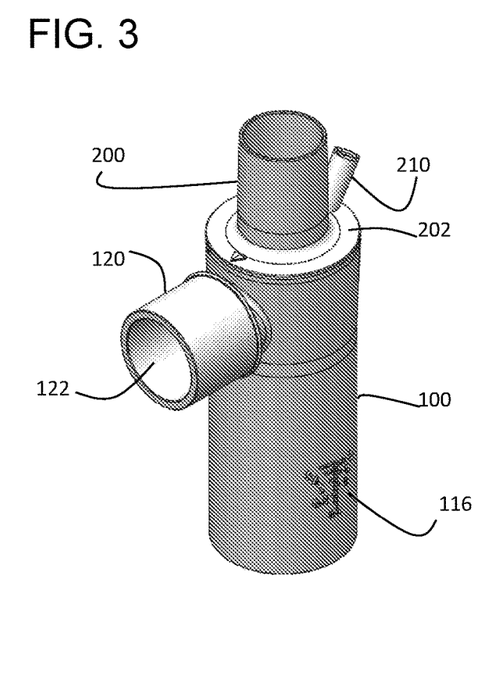
FIG. 3 is an external view of the inventive nebulizer
Figure 4:
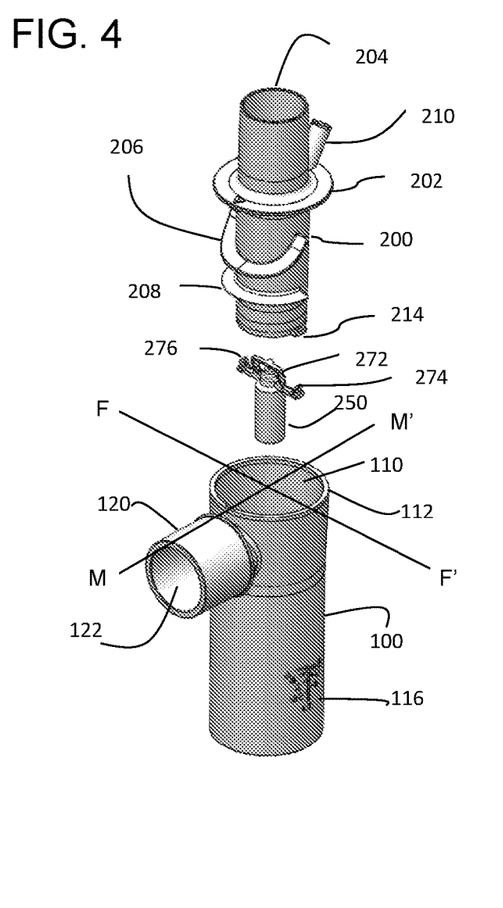
FIG. 4 is an exploded view of the inventive nebulizer, including coordinate system lines M-M' and F-F'.

FIG. 3 shows an exterior view of an embodiment of the inventive nebulizer, having a cylindrical body 100 with an inlet port 204 and outlet port 120. In operation, the inlet port would be in fluid communication with the inspiratory port of a mechanical ventilator. The connection to the mechanical ventilator may be via a gas conduit directly or indirectly connected to the inspiratory port of a mechanical ventilator. In an embodiment, a humidifier may be interposed between the nebulizer and the mechanical ventilator (FIG. 12). In addition, one or more valves such as 3-way valves may be present defining between the inlet port of the nebulizer and the mechanical ventilator as part of a complete breathing circuit, as may be described in co-pending patent application [ ] based on U.S. Patent Application 62/681,654, filed Jun. 6, 2018. Also shown in FIG. 3 are liquid inlet port 210 and markings 116 on the exterior of the nebulizer that assist technicians in filing the nebulizer with the drug solution.

In an embodiment, the nebulizer in this invention is a jet nebulizer, in which a Venturi effect from a flow of air over a liquid channel in fluid communication with a reservoir of a solution of a drug draws the solution through the tube. When the liquid from the drug solution exits the draw tube, it is atomized (also termed aerosolized or nebulized) by shear forces from the air flow. In an embodiment, a baffle may be present to help break up large particles. Ideally, aerosol droplets for inhalation of a drug are in the 2-10 µm size range. Larger droplets tend to stick to the apparatus or mouth and throat of the patient, which is undesirable and causes drug loss.

The exemplary nebulizer has a cylindrical nebulizer body 100 with an upper opening 110 and upper rim 112, a side outlet port 120 with the port opening 122. As defined herein, the descriptors "upper," "top," "bottom," and "lower" are as illustrated in FIGS. 3-10. The inventive nebulizer is intended to be used in a generally vertical orientation with the top and bottom as shown in FIGS. 3-10.

In an embodiment, the lower end of the nebulizer body 100 has liquid reservoir 130, a nebulizer air inlet 140, and a nebulizer air jet 260. The liquid reservoir 130 (FIG. 5) is defined by basin walls 132. The reservoir contains a drug solution liquid 131 suitable for nebulization and is typically charged with 3-6 mL of solution. Such solutions are well known in the art and may include bronchodilators such as albuterol (also called salbutamol in some countries) and other drugs in a sterile, pH controlled, isotonic solution. Other drugs commonly used in nebulizers include anti-inflammatory drugs (see e.g., G. S. Gaude and S. Nadagouda, "Nebulized corticosteroids in the management of acute exacerbation of COPD," Lung India. 2010 October-December; 27(4): 230-235, doi: 10.4103/0970-2113.71957: PMCID: PMC2988175; PMID: 21139721) and antibiotics (see e.g., Bradley S. Quon, Christopher H. Goss, and Bonnie W. Ramsey, "Inhaled Antibiotics for Lower Airway Infections," Ann Am Thorac Soc. 2014 March; 11(3): 425-434. doi: 10.1513/AnnalsATS.201311-395FR; PMCID: PMC4028738).

For example, antibiotics in use for severe respiratory infections of patients breathing with mechanical ventilation include colistin, 75-150 mg administered twice per day; aztreonam, 75 mg administered three times per day; tobramycin, 300 mg administered twice per day; gentamicin, 80 mg administered twice per day, and vancomycin. In an embodiment, an antibiotic treatment may be 6 mL of a solution containing 240 mg gentamicin and 360 mg vancomycin. Other antibiotics are listed in the Quon reference cited above. Clinical indications include cystic fibrosis (CF) chronically colonized with *Pseudomonas aeruginosa*, non-CF bronchiectasis; ventilator-associated pneumonia caused by gram-negative bacteria, and post-lung transplantation. Experimental indications, for which clinical trial data is currently lacking, include tuberculous (TB) or nontuberculous mycobacterial (NTM) lung disease, and chronic obstructive pulmonary disease.

Other exemplary drugs that may be used with the inventive nebulizer include epoprostenol, indicated for acute respiratory distress syndrome (ARDS) and pulmonary hypertension, which may be used in a continuous infusion dose titrated from 1-10 mL/hr of 30,000 ng/ml. Another embodiment is albuterol 2.5 mg mixed with ipratropium 0.5 mg in 3 mL of solution.

As shown in FIGS. 3-11, the breathing gas flow in the inventive nebulizer moves from inlet port 204, then downward in inlet channel 220 defined by internal body 200 (referred to elsewhere as a "chimney" or "flue") to the nebulization area in the vicinity of nebulizer air jet 260. In an embodiment, the airflow entering inlet port 204 is from a mechanical ventilator. In an embodiment, a humidifier may be interposed between the ventilator and inlet port 204.

The drug is nebulized by the nebulizer air jet (as described elsewhere herein) and flows downward through annular gas channel 222 (FIG. 8) to the post-Venturi region 152. At this stage, the nebulized drug suspended in air travels upward in aerosol channel 150 defined by the exterior of internal body 200 and the interior wall of housing 100. Several baffles 206 and 208 direct the flow and help ensure that only appropriately sized droplets proceed to port 124 that directs the air-flow to outlet port 120 and outlet port opening 122.

In an embodiment, the nebulizer air inlet 140 is connected to an air supply 436 (FIG. 12) that provides compressed air at about 50 psi, referred to herein as the "nebulizer air supply." This pressurized air drives the primary Venturi and nebulization will not occur without the nebulizer air active.

The nebulizer air drives nebulizer air jet 260 which creates the primary Venturi effect in the inventive nebulizer. The air jet 260 creates a low-pressure zone from a Venturi effect in the vicinity of the jet orifice. This low pressure draws the drug solution 131 in reservoir 130 through an annular liquid channel 255 defined by the exterior wall of air inlet 140 nested in lower body 250. The drug solution enters channel 255 at channel inlet 254 and travels up the channel 255 from the force of the reduced pressure created by the Venturi from nebulizer air jet 260. The drug solution exits channel 255 at liquid jet 262, essentially an annular orifice surrounding the nebulizer air jet.

Figure 11:
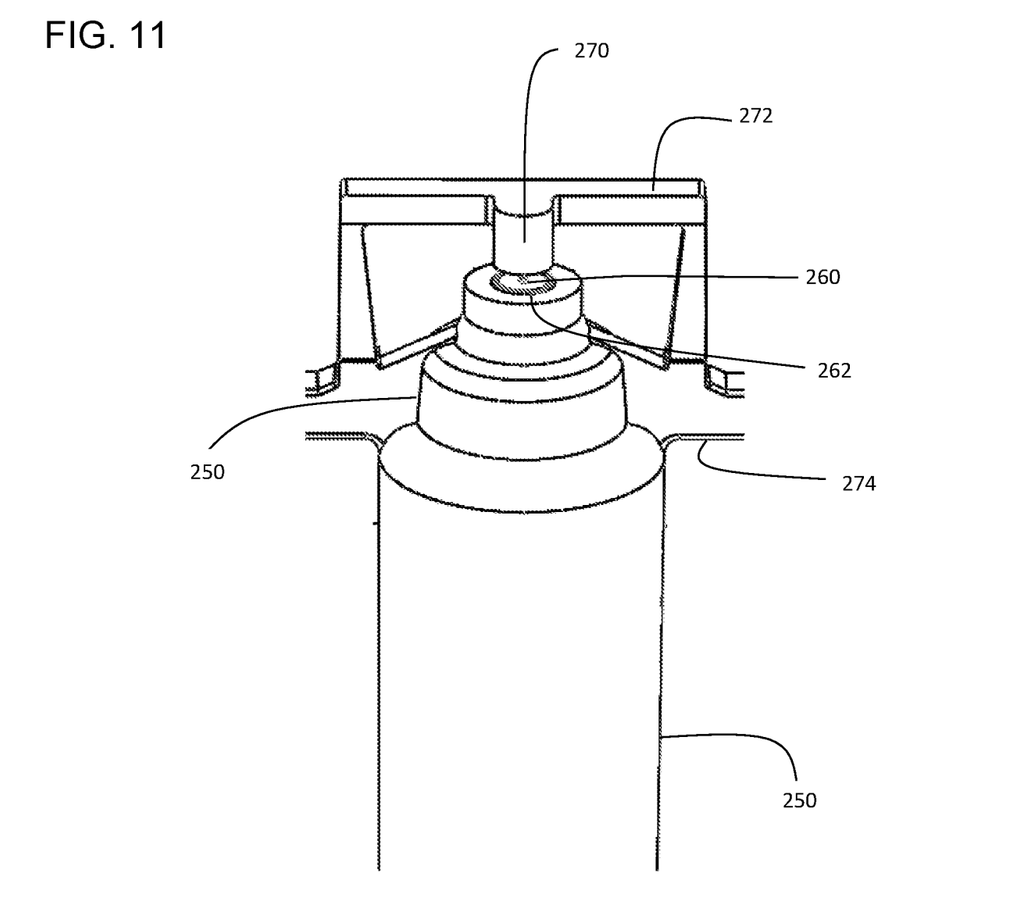
FIG. 11 is a detail of the nebulizer air jet.

A detailed view of the nebulizer air jet is shown in FIG. 11, showing the air jet 250, the annular liquid orifice 262, and baffle 270.

The drug solution, upon exiting the liquid jet 262, will be nebulized by shear stress forces from the air jet. A baffle 270, supported by baffle bracket 272, which may be integral with the lower body 150, amplifies the shear forces to nebulize the drug solution. Ideal nebulized droplets are less than 10 µm in diameter. Moreover, the baffle assists larger droplets, >10 µm in diameter, to return to the drug reservoir 130. Such larger droplets, if they survive past region 152, will tend to stick to walls of the nebulizer, or walls of the ventilator hoses, or if they survive to the mouth and throat of the patient, will tend to stick to interior surfaces before getting into the lungs. Moreover, the reversal of nebulized solution flow direction in region 152 also assists in larger nebulized droplets to return to reservoir 130, since these larger droplets are less likely to be carried upward through passage 150 by the airflow in the nebulizer after region 152. Larger nebulized droplets are undesirable. The objective of nebulization is to make small droplets that stay suspended in the breathing air until arrival at the lower respiratory tract.

The nebulized flow is directed upwards in annular passage 150 after region 152.

Baffles 206 and 208 further assist in capturing oversized droplets by directly impinging oversized droplets, in addition to creating localized turbulence that will contribute to filtering out oversized droplets.

The nebulized airflow is then directed to port 124, which is a perforation in the wall of nebulizer housing 100 that directs the nebulized airflow to outlet port 120 and outlet opening 122, and then to a patient interface for delivery of the nebulized flow to the lungs of a patient. In an embodiment, the nebulized flow is directed to an endotracheal tube implanted in the lungs of a patient in need of assisted breathing.

Figure 7:
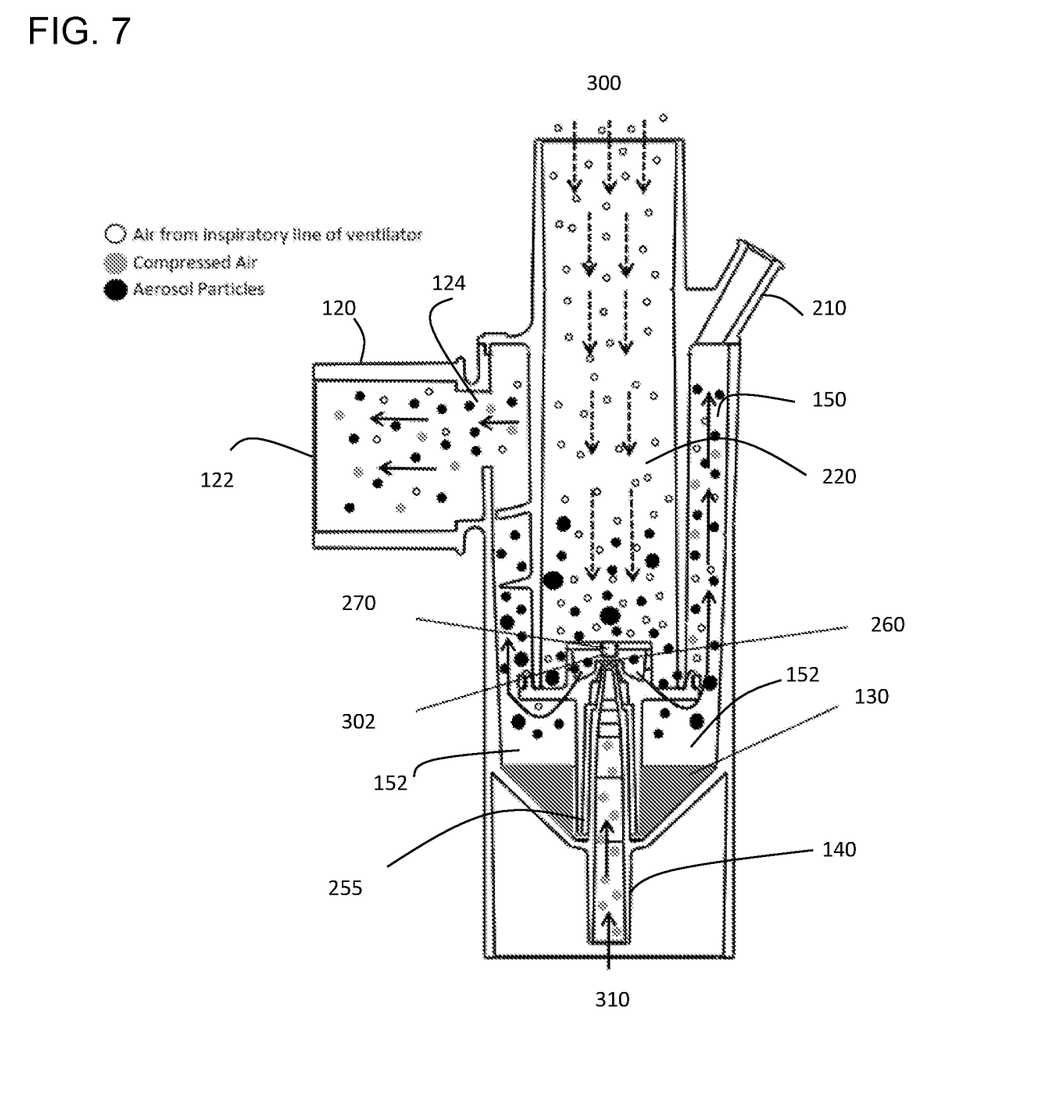
FIG. 7 is a view of the operation of the nebulizer, front view cutaway. The same cross section as FIG. 5.

FIG. 7 shows a cross-section with an operational view of the inventive nebulizer, showing breathing gases 300 entering the inlet port, then flowing past the Venturi where nebulization of the drug occurs, and into region 152. The breathing gas flow is downward up to region 152, but then reverses course and the breathing gases with suspended nebulized droplets is then forced upwards. The breathing gases with suspended nebulized droplets move around internal body 200 and pass through port 124 into outlet port 120 and on to the patient.

Figure 1:
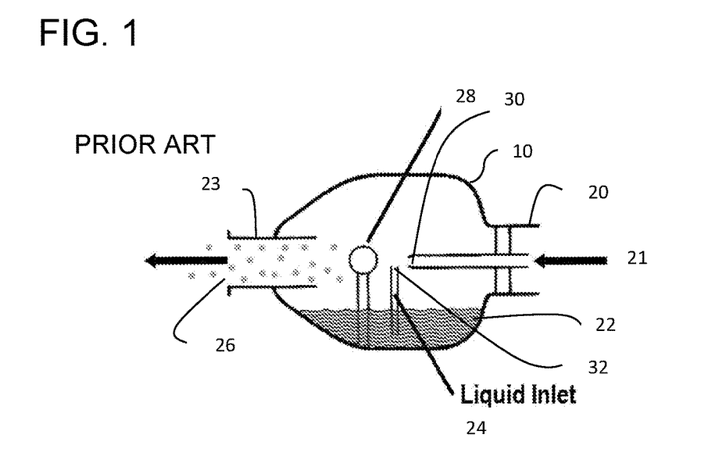
FIG. 1 is a schematic of generic prior art nebulizer.
Figure 2:
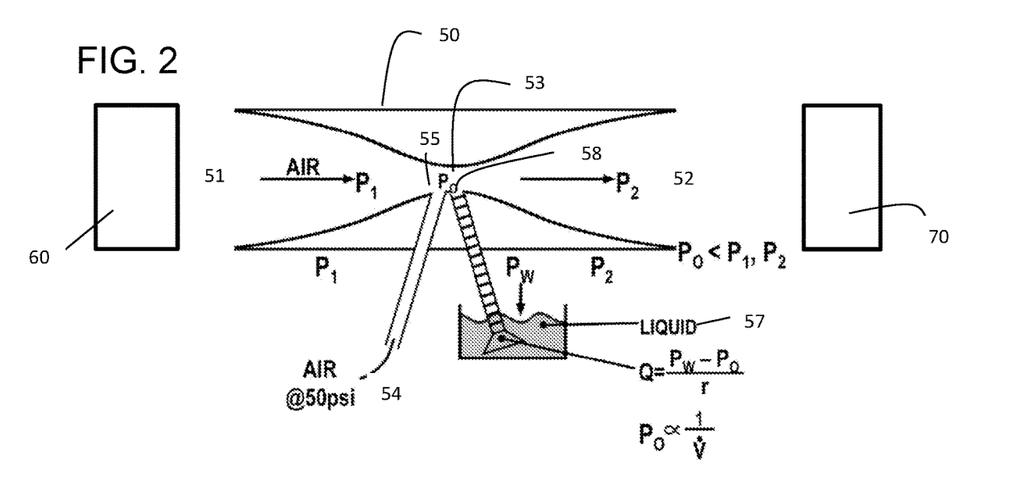
FIG. 2 is a schematic of the inventive nebulizer.
Figure 8:
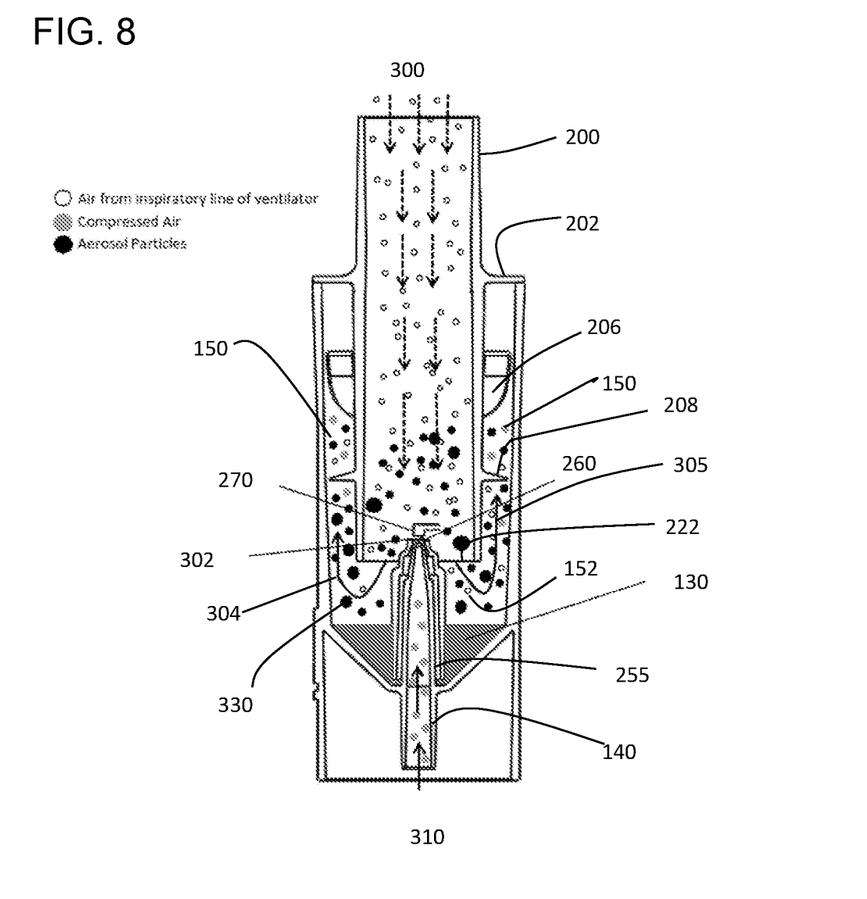
FIG. 8 is a view of the operation of the nebulizer from a side cutaway, sliced along a frontal plane F-F'. The view is from M' to M (see FIG. 4 for coordinate lines).

FIG. 8 is an alternative view of the nebulizer apparatus undergoing the same process as shown in FIG. 7. In particular, annular gas channel 222 is illustrated more clearly in this view demonstrating the flow of gases from the Venturi region to post-Venturi region 152. Annular gas channel 222 is effectively the constriction 53 in the breathing gas channel shown in FIG. 2.

Figure 9:
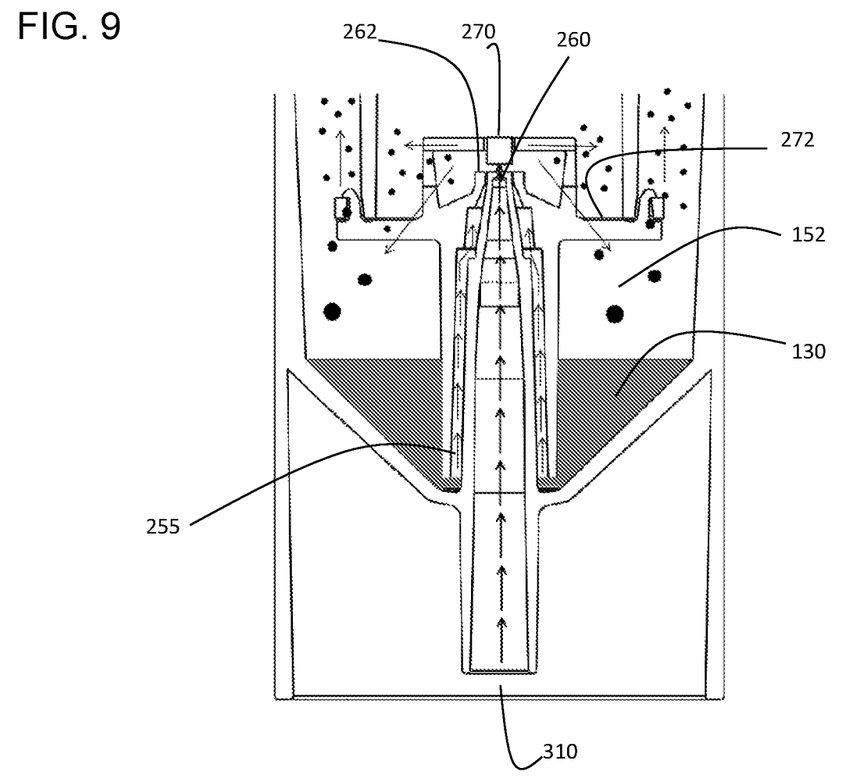
FIG. 9 shows a detail view of the nebulizer in operation. Same cross section as FIG. 5.

FIG. 9 is a detail view of the Venturi and post-Venturi region of the nebulizer in operation, showing the air and nebulized droplet flow away from the Venturi. The droplets are directed past arms 272, which help define passage 222 (FIG. 8). Passage 222 is equivalent to constriction 53 in FIG. 2. The breathing gases with atomized droplets turn around in region 152 and move up passage 150 to exit the nebulizer and on to the patient.

Figure 10:
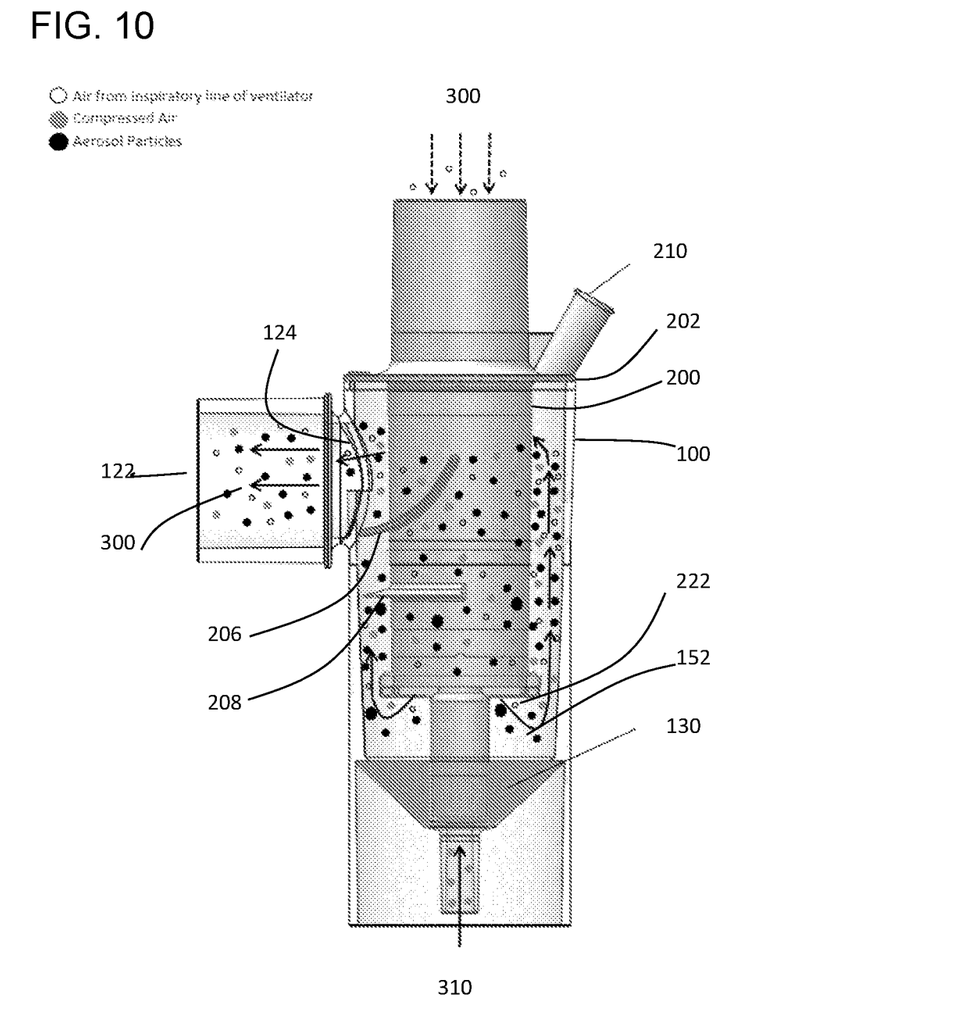
FIG. 10 shows the operation of the nebulizer during nebulization but without inhalation. This is a partial cross-section in the same view as FIG. 5, but the internal body is intact and not cut away.

FIG. 10 is a view with exterior 100 cutaway and the internal body 200 intact, showing the breathing gases with suspended nebulized droplets moving around internal body 200, and passing through port 124 into outlet port 120 and on to the patient.

The inventive nebulizer may be operated continuously or in breath-actuated mode.

Breath-actuated mode is described above and relies on a pressure sensor to toggle the nebulizer air flow and concomitant nebulization on or off. Note that despite the breath-enhancement feature of embodiments of this invention, nebulization will not occur without the nebulizer air flow driving the nebulizer air jet. Nebulizer air flow is typically supplied by a compressed air source at 50 psi, that may be further regulated to provide an air flow at the nebulizer jet of 2.0 L/min or 3.5 L/min, but other flow rates are possible also.

In the continuous mode, nebulization is happening at all times and is not dependent on the inhalation phase of the breathing cycle. For certain drugs or medical conditions, this treatment mode may be desirable. In continuous mode, the pressure sensor, if present, would not be used to toggle the nebulizer air flow. The nebulizer air will flow at all times.

Figure 5:
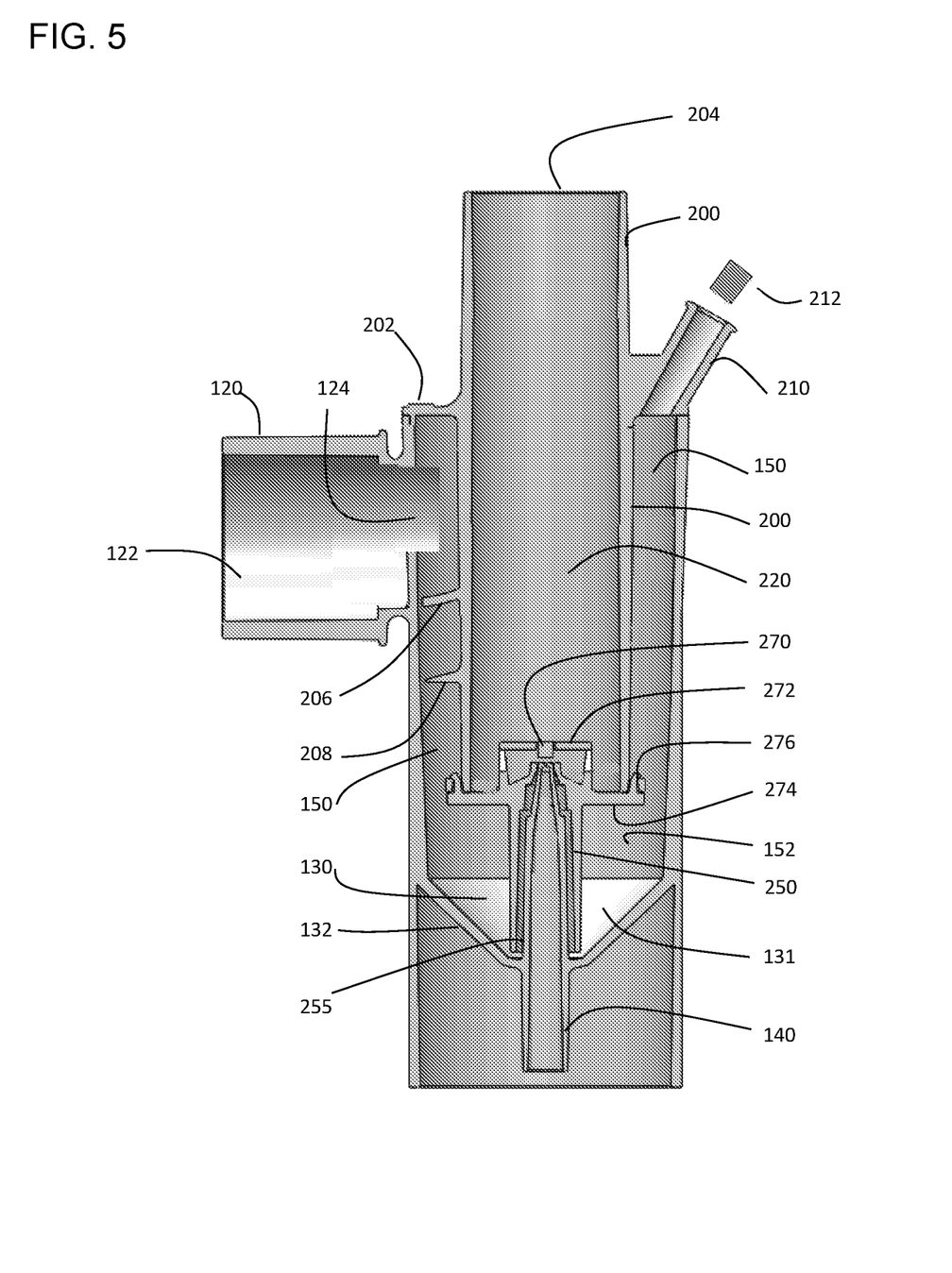
FIG. 5 is a cross-section of the inventive nebulizer, sliced along a medial plane M-M'. The view is from F' to F (see FIG. 4 for coordinate lines).
Figure 6:
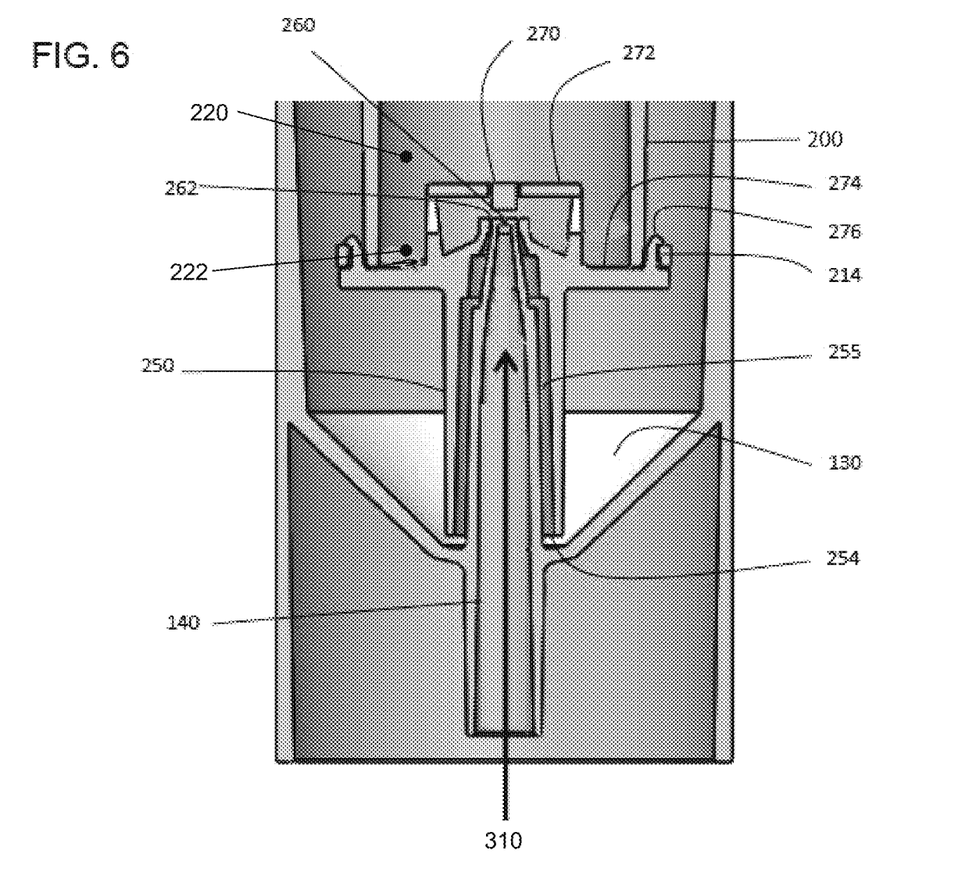
FIG. 6 is a detail view of the Venturi section of the nebulizer, same cross section as FIG. 5.

In an embodiment, a port (210 in the Figures) may be provided to allow a nebulizable drug solution to be added to the drug solution reservoir continuously. For certain drugs such as antibiotics, bronchodilators, and vasoactive drugs, this treatment mode may be desirable. The capacity of the drug reservoir is normally 6 mL and is typically charged with 3 mL or 6 mL of a drug solution. In continuous mode, about 0.5-3 mL of drug solution will be maintained in the reservoir at all times, by continuously adding drug solution through port 210. In an embodiment, this continuous addition mode will be used with continuous nebulization, i.e., not breath-actuated nebulization. This may desirable assuming that a syringe pump (or similar device) is used to continuously add the drug solution at a steady rate to the reservoir. By using continuous nebulization, there will be no dependency on the rate of breathing. The nebulization of drug will be steady and highly predictable. A plug 212 may be provided when the continuous addition port is not in use to stop port 210 (FIG. 5).

In an embodiment, the breath-enhanced nebulizer, such as disclosed herein, may be part of a mechanical ventilator and a breathing circuit as disclosed in FIG. 12. Prior art breath-enhanced nebulizers have until now only been used with spontaneously breathing patients. FIG. 12 shows a representative breathing circuit taken from the inventor's U.S. Patent Application 62/850,728 filed May 21, 2019, and shows a mechanical ventilator (60), a patient (70) (for experimental purposes, a mechanical lung apparatus may be used), and a ventilator circuit with an inspiratory limb (400) and expiratory limb (410). Nebulizer 100 is shown on the inspiratory limb, interposed between T-fitting 402 and three-way valve 403. In this embodiment, humidifier 404 is interposed between the nebulizer and the mechanical ventilator. Pressure sensor 430 is in electronic communication with solenoid valve 432 that toggles nebulizer air supply 434 (at about 50 psi) on or off in air supply hose 436. The three-way valve 403 and T-fitting 402 allow the nebulizer to be bypassed or part of the inspiratory limb of the breathing circuit.

In operation, the nebulizer can be used in a continuous nebulization mode without regard to the inhalation portion of the breathing cycle. In this mode, the pressure sensor and associated toggling of compressed nebulizer air required for nebulization will not be used. Rather, the compressed nebulizer air will be supplied at all times until the drug reservoir 130 (FIG. 5) is empty. In the breath-actuated mode, the pressure sensor 430 is used to detect an increase in air pressure from the ventilator 60 during the inhalation portion of a breathing cycle. This pressure increase triggers the solenoid 432 to switch on the compressed nebulizer air in hose 436 to the nebulizer, causing nebulization to occur. When the patient stops inhaling under the control of the ventilator or is exhaling, the pressure at pressure sensor 430 decreases and the solenoid switches off the flow of compressed nebulizer air in hose 436, and there is no nebulization. By the use of pressure sensor 430 in the position shown, the breath-actuation control is completely independent of the brand or type of ventilator 60. Any ventilator will ultimately have the same function of increasing air pressure in the inspiratory limb during the inhalation portion of the breathing cycle, so this simple expedient is not dependent on any special ventilator feature.

The present inventors have found that breath-enhanced nebulizers, such as those disclosed in this invention, can significantly increase the fraction of drug that is inhaled by the patient and delivered to the lungs (as measured by an inhaled mass (IM) filter in a test apparatus). Moreover, the breath-enhancement feature can significantly shorten the time required to nebulize a particular dose of medication. This can be a significant advantage to the care facility.

Figure 13:
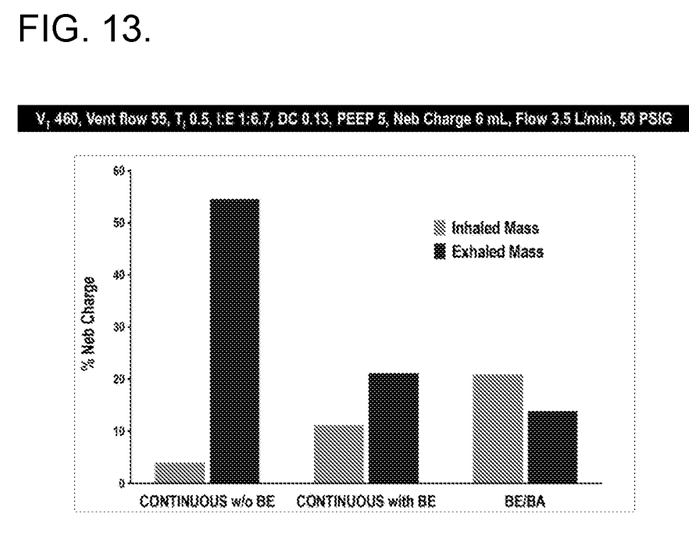
FIG. 13 is a bar graph showing that breath-enhanced and breath-actuated nebulization significantly improves drug delivery to the lungs.

The advantages of the inventive apparatus are shown in FIG. 13. The first two bars show drug flow from a prior art continuous nebulizer without breath-enhancement. The vast majority of the drug is found in the exhaled mass, which is essentially wasted drug. A significant improvement is seen by using a breath-enhanced nebulizer, even with continuous flow. The percentage of drug in the exhaled mass is much lower. Better still is the third set of bars, showing nebulization with breath-enhancement and breath-actuation. In this experiment, the majority of the drug is in the inhaled mass, which measures nebulized suspension that would be delivered to the alveoli in the lungs.

Figure 14:
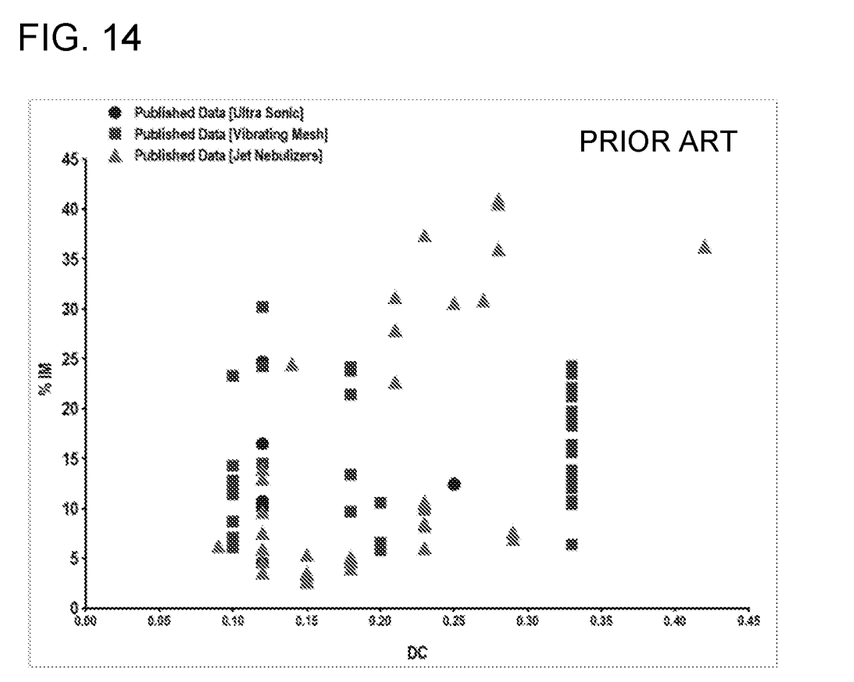
FIG. 14 shows drug delivery rates of several prior art nebulizers.
Figure 15:
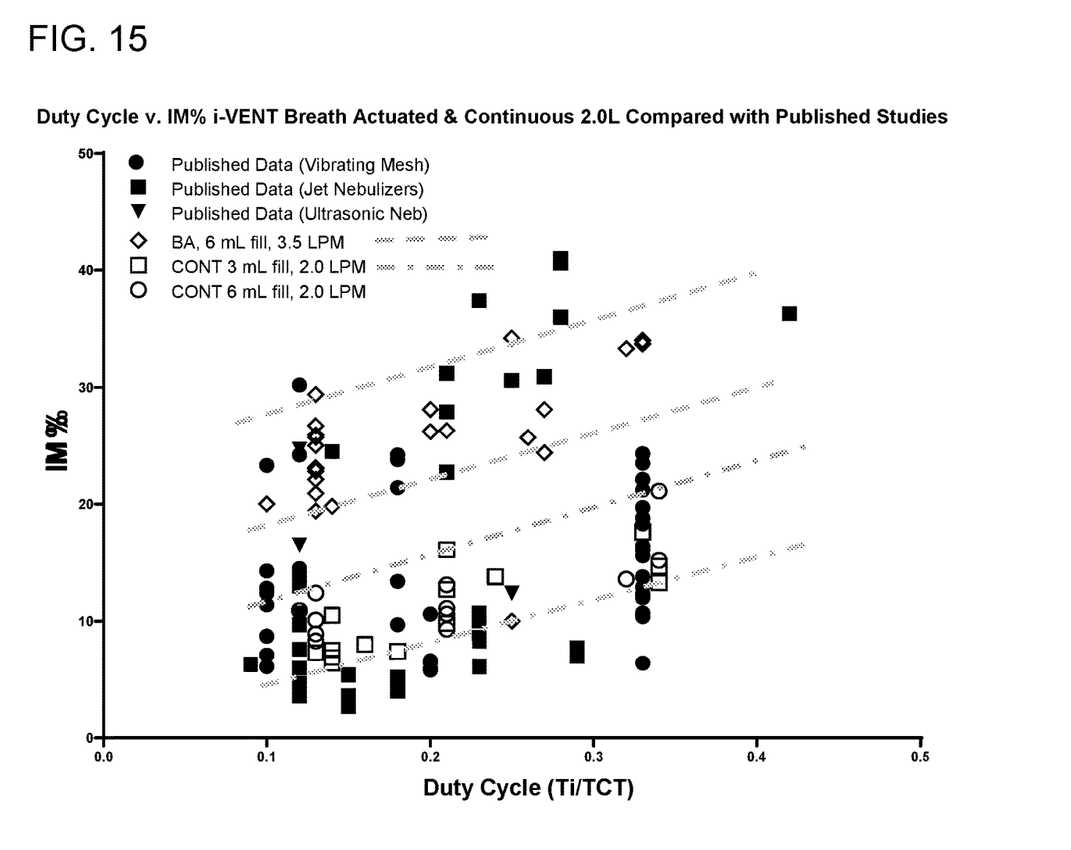
FIG. 15 shows drug delivery rates of the inventive breath-enhanced and breath-actuated nebulizers, marked "i-Vent," superimposed on drug delivery rates with various prior art nebulizers, showing much more consistent flow rates. "BA" is breath-actuated nebulization, measured at 3.5 L/min nebulizer air flow rate and 6 mL fill in the reservoir. "Cont" is continuous nebulization, measured at a 2 mL/min nebulizer air flow rate, and 3 or 6 mL fill in the drug reservoir. Two bands of dashed lines, one for the breath-actuated mode, and a second for the continuous mode, show approximate boundaries that can be expected with the inventive nebulizers.

The instant invention also provides a more reliable and consistent delivery of drug flow. Prior art nebulizers in the inventive ventilator circuit are shown in FIGS. 14 and 15. FIG. 14 shows data assembled by the inventor from several published papers on inhaled mass (% IM) vs. duty cycle (DC; the fraction of the inhalation cycle in which the simulated patient is inhaling), showing considerable variability. These data are all for flow rates of 3.5 L/min (nebulizer air flow) and 3 mL of drug solution in the nebulizer. It can be seen, for example, at a DC of about 0.30, that the % IM ranges for prior art jet nebulizers vary from about 6% to about 42%. This is a very wide range, and undesirable.

FIG. 15 shows data for the inventive nebulizer ("i-Vent" in the chart) superimposed over the data of FIG. 14. Data for breath-actuated ("BA") nebulization, with 6 mL of solution and 3.5 L/min nebulizer air flow rate is shown. Also shown are data for continuous ("CONT") nebulization, at 2.0 L/min nebulizer air flow and 3 mL or 6 mL of drug solution. Bands are shown of the ranges of % IM that can be expected, and it is apparent that these are significantly narrower ranges than for the prior art nebulizers. An upper band of dashed grey lines shows the approximate range of variation for the breath-actuated mode and shows an approximately 10% variability across the range of duty cycles. A lower band of dashed-dot lines shows the approximate range of % IM for the continuous nebulization modes, which were fairly similar for both 3 mL fill and 6 mL fill of nebulizer solution. The lower band likewise shows an approximately 10% variation of % IM over the range of duty cycles studied. This data shows the scatter of variation is much narrower for the inventive i-Vent nebulizers, showing more consistent and predictable dosing providing the inventive nebulizer.

Thus, breath-enhanced nebulization improves control of aerosol delivery during mechanical ventilation. Breath-enhanced nebulization delivers appropriate doses of potent drugs without breath-actuation. Breath-enhanced nebulization plus breath-actuation may deliver high doses of less potent drugs reliably and consistently.

| LEGEND FOR DRAWINGS | |
|---|---|
| Item No. | Description |
| 10 | Prior art nebulizer |
| 20 | Inlet limb |
| 21 | Nebulizer air inlet |
| 22 | Liquid reservoir |
| 23 | Inspiratory (outlet) limb |
| 24 | Liquid inlet |
| 26 | Aerosol outlet |
| 28 | baffle |
| 30 | Air jet |
| 32 | Liquid outlet |
| 50 | Schematic nebulizer |
| 51 | Air inlet |
| 52 | Air outlet |
| 53 | Narrowed air channel |
| 54 | Nebulizer air supply |
| 55 | Air jet |
| 56 | Liquid tube |
| 57 | Liquid reservoir |
| 58 | Liquid outlet |
| 60 | Mechanical Ventilator |
| 70 | Patient |
| 100 | Nebulizer body |
| 110 | Upper opening of nebulizer body |
| 112 | Top rim of the body |
| 114 | Interior of nebulizer body |
| 116 | Markings on exterior of nebulizer bod |
| 120 | Outlet port |
| 122 | Outlet port opening |
| 124 | Port from housing interior to outlet port channel |
| 130 | Liquid reservoir |
| 131 | Drug solution |
| 132 | Basin defining the liquid reservoir |
| 140 | Nebulizer air (50 psi) inlet |
| 150 | Aerosol channel in main body |
| 152 | Post Venturi region |
| 200 | Internal body |
| 202 | Annular ring sealing top of the main body |
| 204 | Inlet port |
| 206 | Upper internal baffle |
| 208 | Lower internal baffle |
| 210 | Input port for continuous addition of the drug to a reservoir |
| 212 | Plug for input port 210 |
| 214 | Baffle support interface |
| 220 | Inlet channel |
| 222 | Annular gas channel having a constriction |
| 250 | Lower body |
| 254 | Liquid channel inlet in the reservoir |
| 255 | Annular Liquid channel |
| 260 | Nebulizer air jet |
| 262 | Liquid jet in Venturi |
| 270 | baffle |
| 272 | Baffle bracket (supports the baffle on the lower body) |
| 274 | Baffle support arm |
| 276 | Baffle interface with an internal body |
| 300 | Inlet air flow |
| 302 | Main venturi |
| 304 | Aerosol flow after Venturi |
| 305 | Aerosol flow after Venturi |
| 310 | Nebulizer air flow |

-continued

| LEGEND FOR DRAWINGS | |
|---|---|
| Item No. | Description |
| 320 | Outlet air flow |
| 330 | Aerosol droplet (various sizes) |
| 400 | Inspiratory limb of the ventilator circuit |
| 401 | Y connector |
| 404 | Humidifier |
| 410 | Expiratory limb of ventilator circuit |
| 420 | Humidifier |
| 430 | Pressure sensor |
| 432 | Solenoid valve |
| 434 | Compressed air supply |
| 436 | Nebulizer air supply hose controlled by the solenoid |

The invention claimed is:

1. A breath-enhanced jet nebulizer adapted for use in administering a nebulized pharmaceutical composition to a patient (70) by inhalation wherein the patient is connected to a mechanical ventilator (60), comprising
   a. a housing (100) in a generally vertical orientation with a breathing gas channel, wherein the breathing gas channel comprises an inlet (204) in fluid communication with a mechanical ventilator (60) and an outlet (122) in fluid communication with a patient interface, and wherein breathing gases (300) flow from the inlet to the outlet (122) when the ventilator is in an inhalation phase of a breathing cycle, and wherein breathing gases (300) from the ventilator (60) are in fluid communication with the inlet (204);
   b. wherein the breathing gas channel is further defined by an internal body (200) nested in the housing (100) such that a flow of the breathing gases has a 180° turn;
   C. wherein the breathing gas channel further comprises a Venturi section in a fixed position relative to the internal body (200) having a constriction (222) in the breathing gas channel, and wherein a nebulizer air jet (260) and a liquid orifice (262) are co-located in the Venturi section, such that the air jet (260) is enclosed within the internal body (200), and wherein the liquid orifice is in fluid communication via a liquid channel (255) with a pharmaceutical composition solution (131) in a reservoir (130);
   d. wherein a nebulizer air flow (310) at the air jet (260) creates a Venturi effect that draws the pharmaceutical composition solution (131) through the liquid channel (255) to the liquid orifice (262) and wherein the pharmaceutical composition solution (131) is directed towards the air jet (260) such that the pharmaceutical composition solution is nebulized by contact with the air jet;
   e. wherein the breathing gases (300), flowing through the constriction (222) in the gas channel (220) during an inhalation enhances the Venturi effect to increase a rate of flow of the pharmaceutical composition solution to the liquid orifice (262); and
   f. wherein the nebulized pharmaceutical composition is carried by the breathing gas flow to the patient interface, and wherein the breathing gas flow through the nebulizer is the exclusive source of breathing gases delivered to the patient from the mechanical ventilator.

2. The breath-enhanced jet nebulizer of claim 1, wherein a baffle (270) is positioned proximal to the air jet (260) and the liquid orifice (262), such that the pharmaceutical composition solution and the air jet are both aimed at the baffle.

3. The breath-enhanced jet nebulizer of claim 1, wherein the patient interface is an endotracheal tube.

4. The breath-enhanced jet nebulizer of claim 1, further comprising a pressure sensor (430) interposed between the inlet inlet (204) and the mechanical ventilator (60), wherein the pressure sensor is in electronic communication with a solenoid valve (432) that controls the nebulizer air flow (310) to the the nebulizer air flow jet (260), such that nebulizer air only flows during an inhalation phase of a breathing cycle.

5. The breath-enhanced jet nebulizer of claim 1, wherein the nebulizer air flow and concomitant nebulization is continuous.

6. The breath-enhanced jet nebulizer of claim 1, wherein a liquid input port (210) is provided for the addition of the pharmaceutical composition solution (131) to the reservoir (130) without stopping nebulization.

7. The breath-enhanced jet nebulizer of claim 1, wherein one or more baffles (206, 208) in a generally horizontal or diagonal configuration are partially wrapped around the internal body (200) within an aerosol channel (150).

8. A method of administering a nebulized drug to a patient breathing with a breathing circuit on a mechanical ventilator comprising nebulization of a drug with the breath-enhanced jet nebulizer of claim 1 and administering the nebulized drug to the patient through the breathing circuit.

9. The method of claim 8 wherein the nebulized drug is a drug for treating bronchospasm in the patient breathing with mechanical ventilation.

10. The method of claim 9 wherein the nebulized drug for treating bronchospasm is 150 mg of albuterol in the pharmaceutical composition solution administered at 12-hour intervals.

11. The method of claim 8 wherein the nebulized drug is a drug for treating mycobacterial infection in the patient breathing with mechanical ventilation.

12. The method of claim 11 wherein the nebulized drug for treating mycobacterial infection is 150 mg of colistin in the pharmaceutical composition solution administered at 12-hour intervals.

* * * * *